United States Patent
Revie et al.

(10) Patent No.: US 9,454,691 B2
(45) Date of Patent: Sep. 27, 2016

(54) METHOD FOR FORMING AN IMAGE REFERENCE DEVICE

(71) Applicant: FFEI Limited, Hemel Hempstead, Hertfordshire (GB)

(72) Inventors: William Craig Revie, Aston Clinton (GB); Martin Philip Gouch, Hemel Hempstead (GB)

(73) Assignee: FFEI Limited, Hemel Hempstead (GB)

( * ) Notice: Subject to any disclaimer, the term of this patent is extended or adjusted under 35 U.S.C. 154(b) by 30 days.

(21) Appl. No.: 14/642,305

(22) Filed: Mar. 9, 2015

(65) Prior Publication Data
US 2016/0004900 A1 Jan. 7, 2016

(30) Foreign Application Priority Data
Jan. 17, 2014 (GB) .................................. 1400815.5

(51) Int. Cl.
| | |
|---|---|
| G06K 9/00 | (2006.01) |
| G01N 1/31 | (2006.01) |
| G01N 21/27 | (2006.01) |
| G01N 15/10 | (2006.01) |
| G01N 15/14 | (2006.01) |

(52) U.S. Cl.
CPC ............. G06K 9/00127 (2013.01); G01N 1/31 (2013.01); G01N 1/312 (2013.01); G01N 21/278 (2013.01); G01N 15/1012 (2013.01); G01N 2015/1465 (2013.01)

(58) Field of Classification Search
CPC ............. G01N 21/29; G01N 15/1012; G06K 9/00127; G06T 7/0018
USPC ........ 356/243.1; 600/476, 473; 422/536, 63, 422/68.1, 547, 501–503
See application file for complete search history.

(56) References Cited

U.S. PATENT DOCUMENTS

| | | | | |
|---|---|---|---|---|
| 5,428,690 A | * | 6/1995 | Bacus | .................... G02B 21/34 356/39 |
| 2008/0314114 A1 | | 12/2008 | Feke et al. | |
| 2011/0318226 A1 | * | 12/2011 | Ge | ....................... G01N 21/278 422/63 |
| 2012/0149050 A1 | * | 6/2012 | Lapen | ............. G01N 35/00029 435/29 |
| 2014/0162245 A1 | * | 6/2014 | Lohse | ...................... C12Q 1/26 435/5 |
| 2015/0192765 A1 | * | 7/2015 | Gouch | ................ G01N 21/278 348/80 |
| 2016/0123850 A1 | * | 5/2016 | Revie | ..................... G01N 1/312 435/40.52 |

FOREIGN PATENT DOCUMENTS

WO 2013/186530 A1 12/2013

OTHER PUBLICATIONS

GB Search Report for corresponding 1400815.5 dated Jun. 26, 2014.

* cited by examiner

*Primary Examiner* — Hoa Pham
(74) *Attorney, Agent, or Firm* — Sughrue Mion, PLLC (57) ABSTRACT

A method is provided of forming an imaging reference device for a biological material imaging system. A first region is provided in a substrate formed from an optically transmissive material which is an analogue of biological tissue. This first region is stained using a first biological tissue stain. A second region is provided in second substrate which is optically transmissive and an analogue of biological tissue. The second region is stained with a second biological tissue stain. The first and second regions are overlapped as a pair, such that light incident upon the pair is modulated by the respective first and second biological tissue stains of the respective regions. Multiple regions of the first and second type may be provided, stained to different degrees.

20 Claims, 9 Drawing Sheets

METHOD FOR FORMING AN IMAGE REFERENCE DEVICE

FIELD OF THE INVENTION

The present invention relates to a method of forming an imaging reference device for use by a biological material imaging system.

BACKGROUND

In histopathology, there are well known methods of examining biological materials such as tissue or cells at microscopic scales. Typical methods used by pathologists for analysing cells involve the preparation of tissue samples by sectioning and staining samples and then examining the stained samples under an optical microscope. Colouring tissue using stains or dyes is a technique commonly used in microscopy to enhance contrast in the microscopic image. Different cell types (or cell components) may be combined with stains of different colours so that they can be easily differentiated. This enables diagnosis of abnormalities or diseases for example.

The set of stains in combination with the method of applying these stains to tissue samples on microscope slides are known as staining protocols. The most widely used staining protocol uses haematoxylin and eosin stains ("H&E" staining). The colour produced by each tissue preparation depends on the type of tissue (or cell component), the tissue thickness and the strength of the stain used. The intensity of the staining depends upon each of the tissue thickness and the stain concentration. This difference in staining strength is important and may influence the diagnostic result a pathologist decides upon.

In modern laboratories it has become common practice to view a sample of cells with a digital camera attached to a microscope or to use a very high resolution scanner to reproduce digitally the appearance of the cells over a larger area. This enables the images to be shared between pathologists without the need for them to be looking down the same microscope at the same sample. A significant problem with this practice, however, is that the colour appearance of the cells has an additional variation added by the colour response of the microscope, digital camera or scanner and the colour monitor or printer being used to view the image, as each of these devices has its own colour response. A means to calibrate and to assess the colour accuracy of these systems is highly desirable.

The variation in colour appearance due to different image capture and reproduction equipment is a problem commonly encountered in colour imaging. This problem is normally addressed by using a standardised calibration process as defined by the International Color Consortium (ICC). This is a standardised way of translating digital values read by a device or equipment into colour measurements defined by the Commission Internationale de l'Eclairage (CIE). The ICC defines a file format which specifies a mathematical transform that can be used to convert the device colour values to colour values in an interchange space that uses device independent CIE colour coordinates. Thus a colour produced by one image capture device or reproduction device can be mapped onto another device such that to a typical person they appear to be the same colour. This file format is commonly referred to as an "ICC profile".

In the graphic arts, an ICC profile is generated by producing matched pairs of values. The reproduction part of the process, i.e. by monitor display or printing, is common in the graphic arts and in a similar way ICC profiles can be used with the reproduction of microscopy images. Typically an input device such as a graphic arts scanner or a studio camera is calibrated or characterised using a colour calibration target. The calibration target typically contains a set of colour patches having a wide range of colours. The colour patches are imaged with the input device which usually produces three values for each colour patch, commonly called RGB, or red, green, blue triplets. The corresponding colour patches of the chart are then measured with a spectrophotometer or other suitable instrument which typically produces 32 sets of spectral reflectance or transmittance values across the visible spectrum. These spectral values can then be converted to CIE colour coordinates using the equations defined by the CIE, which are typically triplets such as CIELab or CIEXYZ. An ICC profile describes the mapping from the RGB values to the CIE colour values.

The colour patches are normally combined into a mosaic of patches referred to as a calibration chart. Typically this is a chart as defined by ISO 12641:1997 "Graphic technology—Prepress digital data exchange—Colour targets for input scanner calibration", but there are other examples of such calibration charts such as the XRite Color Checker. It is normal for the calibration chart to contain the colours typically presented to the image capture system such as a microscope with an attached digital camera.

For graphic arts applications, these calibration charts are produced in every type of film substrate used in order to ensure that the spectral content of each patch is the same as the spectral content of the images being scanned. Otherwise, a phenomenon known as metamerism can cause the ICC profile to correctly calibrate the chart but to give different colours for the image being scanned. In the case of a digital microscope used in pathology this phenomenon can occur when the same colour on the chart and the stained cell have a different spectral content which produce the same CIE colour value but different imaged RGB values.

One approach to more accurately reproduce the spectral response of biological stains is disclosed by the present applicant in WO2013/186530. That patent publication discloses a method of forming an imaging calibration device by depositing and localising tissue stain material in regions of the device, such as "wells", which are defined within a gasket placed on top of a glass slide.

Despite the methods and apparatus discussed in WO2013/186530, there remains a need to provide improved devices, and methods of their production, which can be used to assess the accuracy with which a digital microscope system is able to reproduce slides stained using a given staining protocol, together with a calibration system for digital microscopes that minimises the effect of metamerism.

It would in principle be possible to use standardised biological tissue samples to address these needs however there are a number of difficulties with this approach:

(a) it is difficult to produce standardised tissue and to produce sections of standard thickness, (b) stained tissue samples exhibit significant variation in colour within a cell and this makes it difficult to obtain regions of uniform colour of a size that can be measured and (c) tissue samples degrade with time resulting in significant colour shifts.

There is therefore a need to identify a non-tissue substrate that can be stained to produce the same colours as biological tissue samples and which may be readily manipulated so as to provide imaging calibration or reference devices for biological imaging systems.

SUMMARY OF THE INVENTION

In accordance with a first aspect of the present invention we provide a method of forming an imaging reference device for a biological material imaging system, the method comprising:

providing at least one first region of a first substrate, the first substrate being formed from an optically transmissive material which is an analogue of biological tissue, wherein the at least one first region is stained using a first biological tissue stain;

providing at least one second region of a second substrate, the second substrate being formed from an optically transmissive material which is an analogue of biological tissue, wherein the at least one second region is stained using a second biological tissue stain; and, overlapping at least one pair of regions, each pair being formed from the overlap of a first region with a second region, such that light incident upon a pair is modulated by the respective first and second biological tissue stains of the respective regions.

We have realised that overlapping two or more optically transmissive substrates, each of which having been stained using a biological tissue stain, enables the production of significantly improved reference devices, which may be used for example as stain colour charts. Stained regions of substrate material provide for ease of handling when forming a reference device. The concept of "stacking" two or more different regions enables many different combinations of stains to be produced readily, for example, either for use of the device in a direct comparison with a similarly stained tissue, or for the use of a device as a calibration device. Thus, substrate materials may be stained and combined on microscope slides to produce sets of standardised colour reference patches that closely match the spectral characteristics of colours present on pathology slides. These colour references can be used to create a calibration slide for digital microscopes and to create reference materials for each staining protocol that can be used to assess the performance of digital microscopes. In its most general form the device may be used as a reference for simple comparison purposes when imaging or viewing a stained tissue sample. However, the device may be used as a more advanced reference device where for example spectral measurements are taken from numerous differently stained regions, having a known staining intensity, and these may then be used as a calibration device to calibrate imaging apparatus.

The first and second biological tissue stains (each herein referred to as "stains") may in fact each be of the same material. They may therefore be of an identical composition. They may also be of different composition, in the sense of different levels of dilution albeit with the same stoichiometry of the stain itself.

In many cases however the first and second biological tissue stains are formed from entirely different stain materials. As an example the first biological tissue stain may be haematoxylin at a given respective composition and the second may be eosin at a given respective composition. A surprising finding from our research in the effect of stains is that stains do not typically interact with each other, at least in the sense of their effect in modulating the spectrum of transmitted light. Hence a staining target (such as biological tissue) which undergoes staining with two different stains, has a similar effect on transmitted light as two such targets stained individually. The fact that the spectral effect of a stain is optically independent allows superposition of spectral effects mathematically and also, crucially, physically.

Hence, unexpectedly we have found that the stacking or overlaying of independently stained regions of substrates is an excellent model for tissue, either in the sense of different intensities of staining using a common stain, or more usefully in terms of tissue stained with two or more different stain types.

We have identified a number of non-tissue substrate materials which can be used as a biological tissue analogue. Such materials are a tissue analogue in the sense that they absorb and retain biological tissue stains in a similar sense to biological tissue. Preferably these materials are manufactured analogues which allows the process by which they are formed to be carefully controlled, this in turn providing the substrates with accurately controlled properties. The stain absorption and retention behaviour also allows substrates manufactured from such materials to be processed and manipulated after staining has occurred since they provide a dry colouration to the material itself. Such materials include, but are not limited to cellophane (RTM), cellulose, agar, agarose and gelatine, that can be used as an effective substrate for pathology stains. Whilst the first and second substrate may comprise different materials, typically the first and second substrate will be a common material, for example cellophane.

Typically such materials are manufactured polymers. They are preferably provided in the form of a film. It is preferred that such a film is self-supporting to enable ease of processing. Films are useful since they are typically produced with a reliably uniform thickness and are sufficiently thing to provide low attenuation of light when in an unstained state. In general, the stains are applied to the substrate by immersing the substrate in a bath of the stain at a predetermined concentration. The stains are generally absorbed by the substrate material such that a homogeneous distribution of staining is achieved in the through-thickness direction.

In the most advantageous practical examples two or more of the first and/or second regions are provided. Typically a plurality of first regions is provided as a first series of first regions and a plurality of second regions is provided as a second series of second regions. The plurality of regions may be thought of as a "series" in terms of a relationship between the respective locations of the regions within the device. Alternatively, or in addition, the series may be in the sense of the respective relative effects of the regions upon the incident light. Preferably in one or each of the first and second series, the respective spectral effects of the stains applied to the regions within a series are modulated. The modulated spectral effects may be produced by using one or more of:

i) different concentrations of the respective biological tissue stains;
ii) different time durations of application of the respective biological tissue stains;
iii) different thicknesses of the regions of the respective first and/or second substrate; or
iv) different stain absorption characteristics of the respective regions of the first and/or second substrate.

The regions within a series may be produced upon a common piece of unitary substrate, such as a piece of substrate film. Typically however regions with different degrees of staining are produced upon different pieces of substrate (for example each being cut from a film) and these are then bonded together so as to form the reference device. The regions themselves may take a number of different geometrical forms. Each region in one or each of the first or second series may be elongate with the directions of elongation being parallel. For example, the regions of the first and the second series may each be arranged to be elongate, with the respective directions of elongation of the first and second series being arranged at an angle such that the pairs of overlapping regions form a two dimensional array. With these directions being orthogonal, a grid pattern of overlapped pairs of regions may be produced in the device. The physical arrangement of the regions within the first or second series may correspond to a monotonical modulation in the effect of the respective staining on incident light. Thus the staining may become increasingly intense across a series for example. In a simple example, this intensity modulation may be linear across a series in terms of its effect upon transmitted light (such as broad spectrum or white light).

The stained regions within a series may be formed by the overlap of corresponding numbers of layers of the substrate, each of similar thickness and staining. Hence for example a series of regions may be produced by overlaying similar pieces of stained material and for example attaching them together to form a unitary item which may be combined with one or more other substrates comprising a second series.

As will be understood, depending upon the desired combination of stained regions, the overlap between two or more regions may be partial or full.

In many cases the first and second biological tissue stains each comprise single stains. However it is contemplated that one or each stain may itself comprise two or more different biological tissue stains. Although the examples described herein are for Haematoxylin and Eosin (H&E) staining, the same techniques can be applied to a wide range of staining protocols including but not limited to the following: Haematoxylin and Eosin (H&E), Diaminobenzidine (DAB) with Haematoxylin counter stain, Papanicolaou (PAP), Perls' Prussian blue, Periodic acid-Schiff (PAS), Reticulin, Millers elastic Van Gieson, Shikata, Giemsa stain, Ziehl Neelsen technique, Grocott, Alcian blue PAS, Jones methenamine silver, Gram, Congo red stain for amyloid and Masson trichrome.

In accordance with a second aspect of the invention we provide an imaging reference device for a biological material imaging system, the device comprising: a first substrate formed from an optically transmissive material which is an analogue of biological tissue, the first substrate having at least one first region stained using a first biological tissue stain; and, a second substrate formed from an optically transmissive material which is an analogue of biological tissue, the second substrate having at least one second region stained using a first biological tissue stain;

wherein the first and second regions are overlapped so as to form a pair of regions, such that light incident upon a pair is modulated by the respective first and second biological tissue stains of the respective regions.

Typically the substrates forming the pairs of regions are bonded together using one of a number of bonding techniques, such as gluing. The reference device also typically comprises a microscope slide to act as a support for the substrates. The slide may in practice contain multiple instances of stained substrates using different combinations of stains.

In accordance with a third aspect of the invention there is provided an imaging reference device produced by the method according to the first aspect of the invention.

BRIEF DESCRIPTION OF THE DRAWINGS

Some examples of the present invention are now described with reference to the accompanying drawings, in which.

DESCRIPTION OF PREFERRED EXAMPLES

Figure 1:
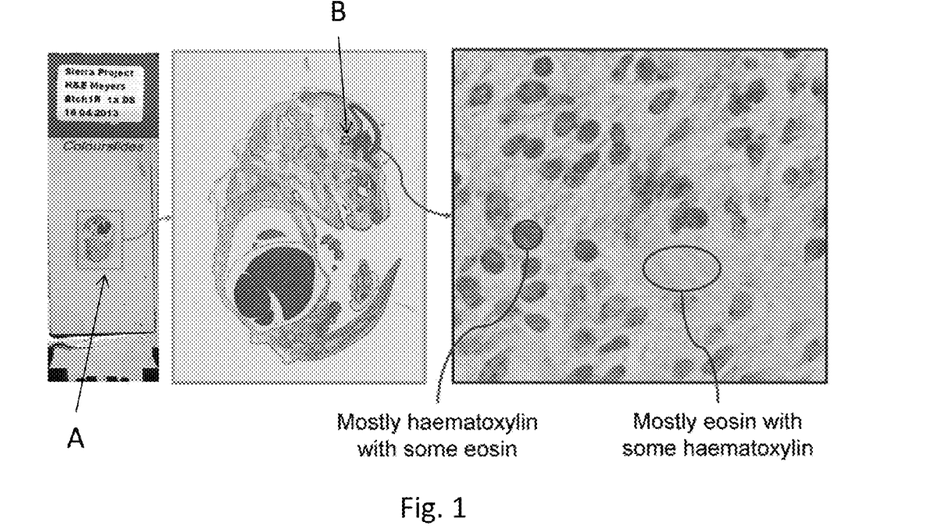
FIG. 1 shows a stained tissue sample at three different levels of magnification.

In order to inspect biological tissue using optical methods, typically combinations of stains are applied to pathology samples (following a staining protocol) in order to enhance the colour contrast between different tissue elements. FIG. 1 shows example images at three different magnifications, where the tissue is stained with haematoxylin and eosin (commonly known as H&E staining). A low magnification image on the left of FIG. 1 shows the stained tissue in question positioned upon a microscope slide. An area "A" of the stained sample is magnified in the central image in FIG. 1. Within this, a further area B is magnified in the image to the right of FIG. 1. In the magnified area B, the cell nuclei are stained strongly, this staining being produced mainly by haematoxylin with a small percentage of eosin. The more lightly stained surrounding elements are stained primarily by eosin with a small amount of haematoxylin. Other levels or staining are produced by differing mixes of the two stains. Example regions are indicated in FIG. 1. As will be appreciated, in practice these different levels of staining are actually represented by different colours, these originating from the two different stains. The different colouration of the tissue allows a pathologist to inspect the tissue using a microscope imaging system so as to obtain information about the structure of the tissue including the presence of abnormalities or disease.

Our investigations in to the way these colours are produced shows that there is usually no chemical interaction between the stains and that the colour produced in any region depends only on the amount of each stain present at each point in the sample. In other words the colours mix in a simple linear fashion. This is illustrated more clearly with reference to FIGS. 2 to 5.

Figure 2:
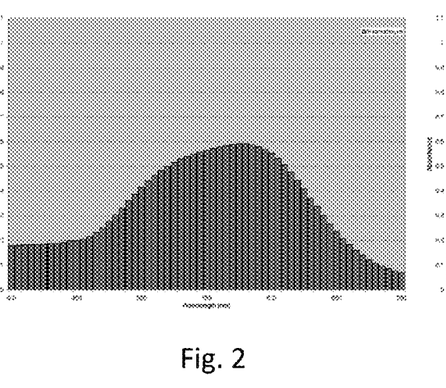
FIG. 2 is a graph of the spectral absorbance for the haematoxylin stain at optical wavelengths (400 to 700 nm)
Figure 3:
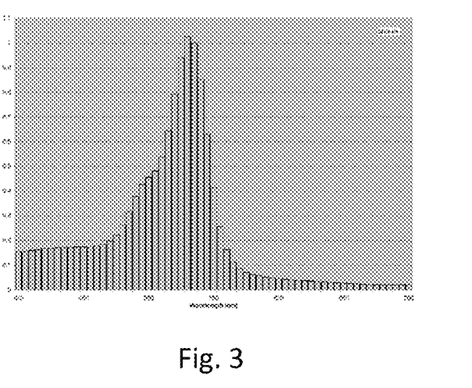
FIG. 3 is a graph of the spectral absorbance for the eosin stain at optical frequencies.
Figure 4:
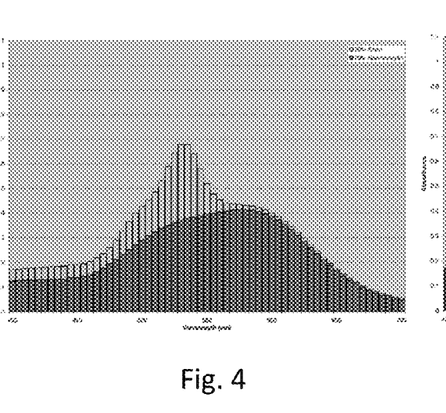
FIG. 4 shows the superposition of a spectrum of 30 parts of eosin to 70 parts of haematoxylin.
Figure 5:
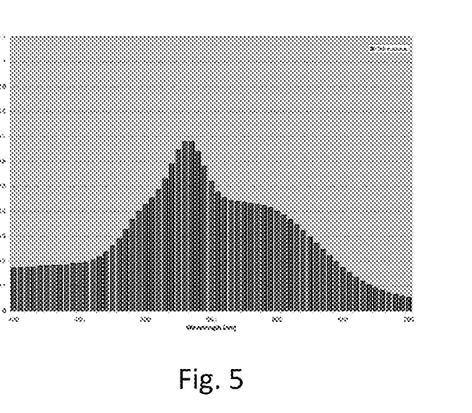
FIG. 5 shows a corresponding spectrum from a 30:70 mixture of eosin:haematoxylin.

FIGS. 2 and 3 show graphs of the spectral absorbance for haematoxylin and eosin stains, respectively, in isolation, measured at a number of wavelengths across the visible spectrum from 400 nm to 700 nm. FIG. 4 shows a stacked bar graph with the spectral absorbance formed from 70% haematoxylin (below and darker in FIG. 4) with 30% eosin (above and lighter) added. FIG. 5 shows a typical measured spectrum for a cell nucleus stained with a 70:30 mixture of haematoxylin:eosin. As can be seen by inspecting FIGS. 4 and 5, the measured absorbance for the cell nucleus is the same as the absorbance of 30% eosin added to 70% haematoxylin. Similarly it is found that other spectra taken at other locations in the tissue of the slide are composed of different percentages of each stain.

Investigation of a number of materials has shown that the stains can be applied to cellophane (or similar materials) to produce a result which is most similar in colour to that of stained tissue. A number of such other similar materials could also be used such as cellulose, agar, agarose, or gelatine providing the optical characteristics are similar to that of cellophane and the stain can be applied effectively. These materials act as effective "biological tissue analogues".

This information can be used in the generation of reference devices.

Figure 6:
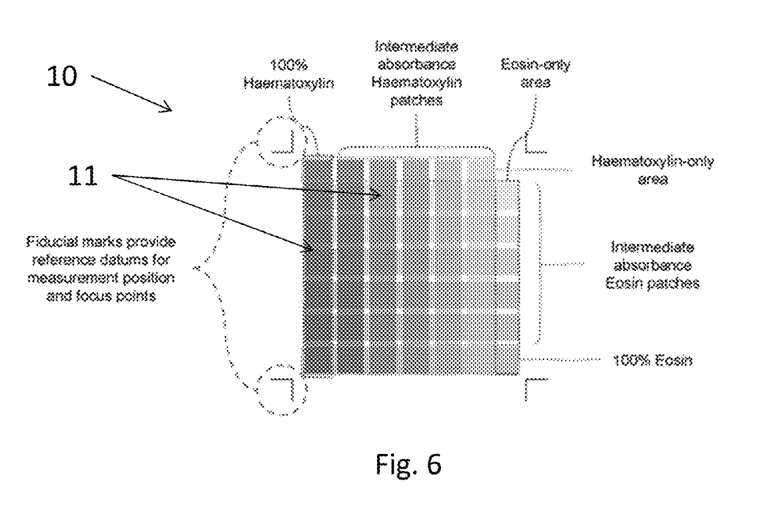
FIG. 6 shows a first example reference device formed from overlapping series of strips of first and second biological tissue stains.

A first example of such a reference device is shown in FIG. 6. The device may be generated using a set of sheets of cellophane which are stained using different strengths of the stains used for each staining protocol. These sets of sheets are cut into strips and then laid on top of each other as shown to produce different colour combinations in each overlapping region. The method of producing the reference device of the first example is now discussed in more detail.

Figure 7:
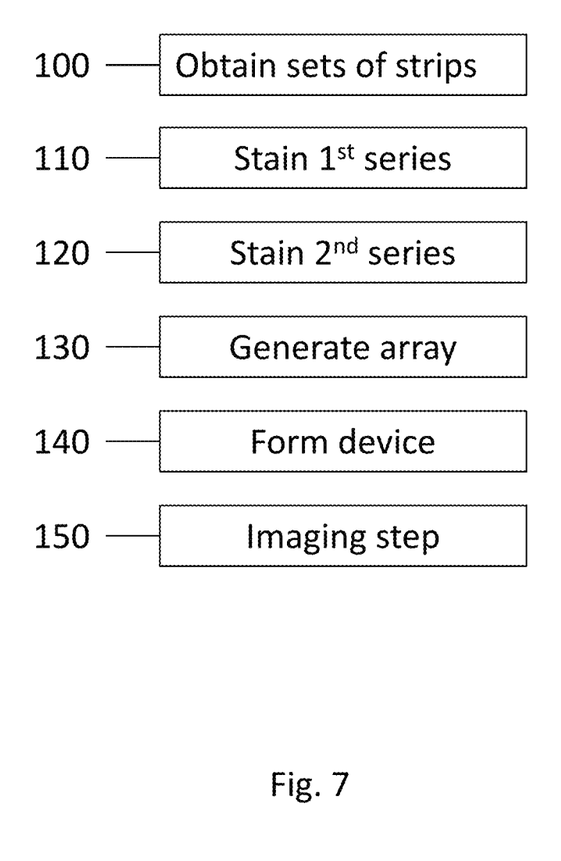
FIG. 7 is a flow diagram of a method of producing a reference device according to a first example.

With reference to FIG. 7, at step 100 a number of similar rectangular cellophane strips are obtained, for example by cutting these from a larger piece of cellophane film. The width of the strips is typically 1-2 mm and the thickness of the film is typically 5-30 micrometers. Half the number of strips is used to form a first series of strips and the remainder a second series. For this example six strips are used in each case. At step 110 the first series of strips is stained using haematoxylin. In each case a strip is fully immersed in a bath of haematoxylin for a given duration (which may be from 10 seconds to 30 minutes). The concentration of the haematoxylin in the bath is modulated for each individual strip. The concentration is carefully controlled such that each strip is stained to a different degree (producing a corresponding staining intensity), this having a corresponding effect on the modulation of incident light which passes through the strip. The duration of immersion in the bath is chosen to be the same in this example. The concentrations of stain used for the different strips range from a minimum to a maximum concentration in equal concentration steps. The minimum concentration is set as a certain percentage (such as 10%) of a predetermined concentration, with the maximum being 100% of that concentration.

Having obtained a first series comprising 6 strips of increasing levels of haematoxylin staining at step 110, a similar procedure is followed on the remaining 7 strips using eosin (note that the time period used for staining with eosin may be different from that of haematoxylin). This is performed at step 120. At step 130 the strips of the first and second series are then arranged in a regularly spaced array with the direction of elongation of the strips being parallel for all strips within a series and the direction of elongation for the first series being orthogonal to that of the second series. This is shown in FIG. 6. The footprint of a given strip which overlies another strip forms a patch 11 which represents the intersection of the component stained regions from the respective strips. The strips are arranged onto a glass microscope slide and adhered in their array configuration with adhesive (using regions of the strips in each case which are not overlaid by other strips) so as to form the first example reference device. It will be noted that the relative arrangement of the strips is such that a small area at one end in each case is not overlapping with any strip from the other series. This allows for regions of only haematoxylin (at its 6 different staining levels) and only eosin (at its 6 different staining levels) to be imaged also. These areas can be seen in the upper and right hand regions of FIG. 6.

As is also shown in FIG. 6, fiducial marks are used to provide reference datums for measurement positions and focus points for use by the biological imaging system in question.

The reference device 10 so formed, therefore has a set of colours produced where the strips overlap to provide (in this case) thirty six patches with different combinations of stain intensity and six patches with different intensities of each stain. In the present example the entire strip in each case is stained using the appropriate stain material. This is convenient for manufacturing purposes but not essential. The stained region may therefore form only part of a particular piece of substrate material if required.

At step 150 in FIG. 7, a biological tissue imaging system, for example including a microscope coupled with an automated stage and colour imaging device, is used to take reference measurements of the colours of the series of regions (overlapping and non-overlapping) of the device 10. These are stored and processed, so as to obtain data relating stain protocol with the spectral response of the regions in question (in terms of red, green and blue data), as imaged by the imaging system. Hence the set of coloured patches for a single staining protocol can be placed on a microscope slide and used to evaluate the accuracy with which a digital microscope is able to reproduce a particular staining protocol.

Although the example shown here is for H&E staining, the same method can be used for all other staining protocols that use two stains. It is of course not necessary to have similar numbers of strips/concentration steps for each series.

The method can be extended for protocols that use more than two stains by adding additional layers for the other stains.

Multiple sets of such coloured patches can be placed on a microscope slide and used in a similar way to graphic arts calibration targets to calibrate a digital microscope system, for example by creating an ICC Profile.

A second example is now described of a manufacturing method that may be used to produce a set of coloured patches for a single staining protocol. This example again describes H&E staining; however sets of coloured patches for other two-stain protocols can be constructed in a similar way.

Figure 8:
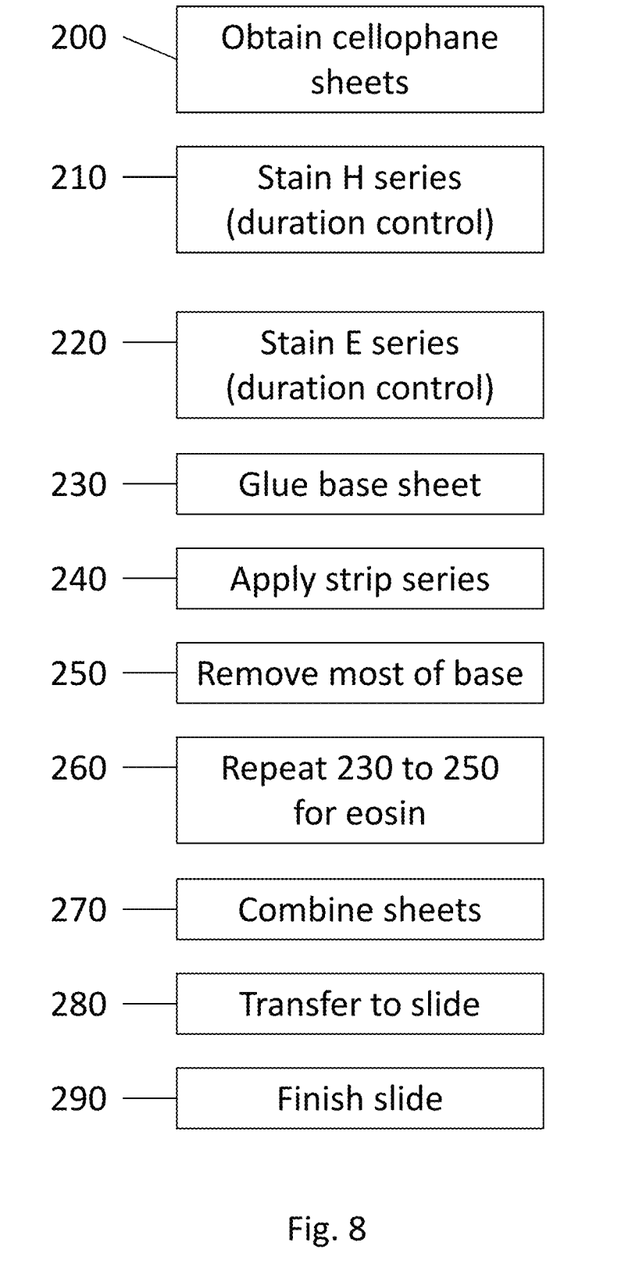
FIG. 8 is a flow diagram of a method of producing a reference device according to a second example.
Figure 9:
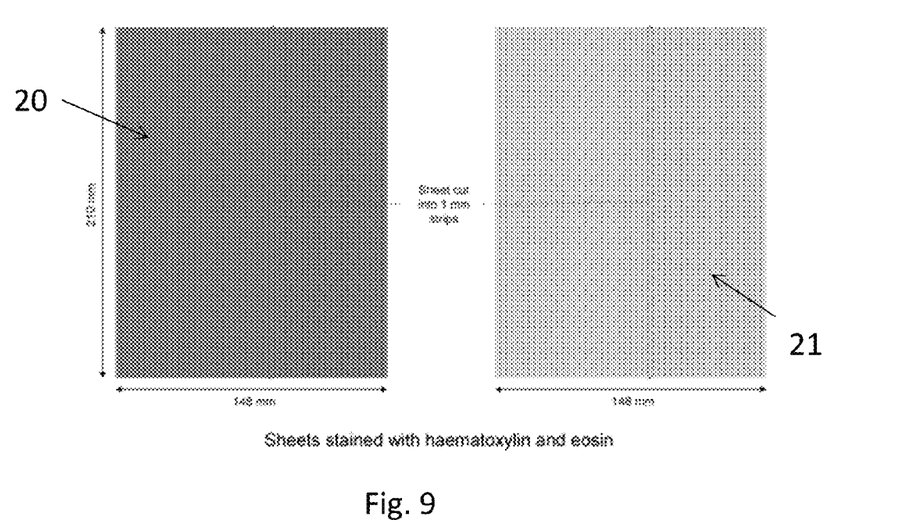
FIG. 9 shows sheets initially stained according to the second example.

With reference to FIG. 8, initially at step 200, a number of sheets of cellophane are obtained having dimensions 210 mm by 148 mm by 5-30 micrometers. At step 210 a set of the sheets 20 is immersed individually in a bath of haematoxylin. The duration used for each sheet is carefully monitored and a series of differently stained sheets is obtained by immersing each sheet for a specific predetermined period so as to provide a series of sheets stained with increasingly heavy staining, in this case the duration ranging from 10 seconds to 10 minutes. An example sheet 20 bearing a haematoxylin stain is shown at 20 in FIG. 9. At step 220 a set of sheets (an example of which is shown at 21 in FIG. 9) is stained using different durations to provide a staining series for eosin. In each of the above cases different concentrations of haematoxylin and eosin may be used (in a similar manner to the first example) as an alternative, so as to provide an increased staining range. As a further alternative, the surface of each sheet may be provided with a layer which affects the rate of absorption of the stain and modified layers upon different sheets may be used to provide the modulation in the degree of staining. There are well known methods for controlling the absorbance characteristics of polymer films using a coating material applied to each side of the film.

Figure 10:
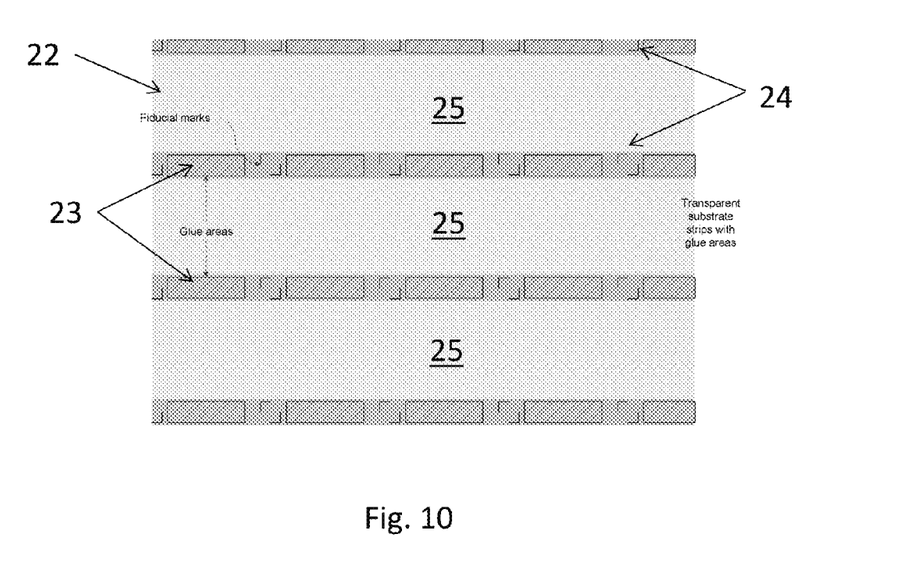
FIG. 10 shows a base sheet with gluing and fiducial marks according to the second example.
Figure 11:
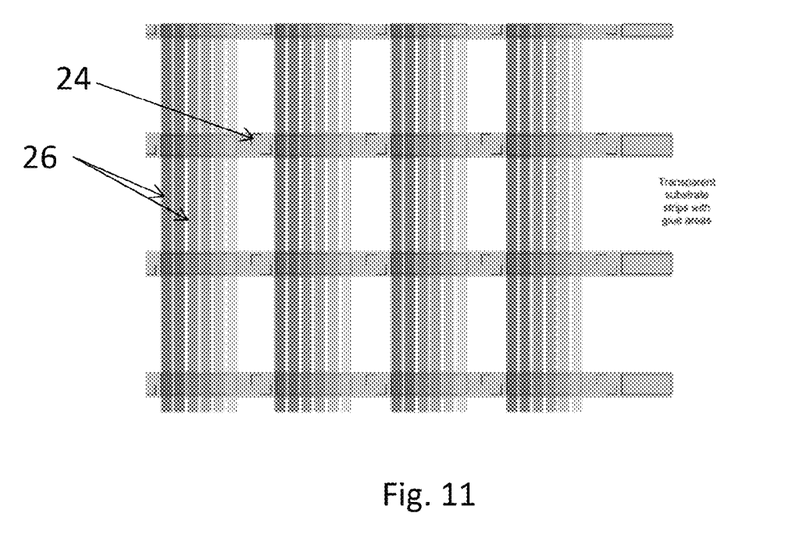
FIG. 11 shows a number of strips applied to the base sheet of the second example.

At step 230 a sheet of unstained cellophane substrate 22 is prepared with rows of elongate, generally rectangular, glue bearing areas 23, these being regularly spaced in a grid on the sheet 22 as shown in FIG. 10. The substrate 22 is also marked (for example by pre-printing) with fiducial marks shown at 24. The light grey regions 25 of the substrate sheet will be removed once the strips have been fixed to the sheet and these regions 25 are partially cut or scored so that they can later be detached. At step 240 1 mm wide strips 26 are cut from the haematoxylin-stained sheets and are applied across the rows of glue-bearing areas 23. In the present case six strips (each from a sheet with a different level of staining) are applied side-by-side as a "series" and the series is repeated four times across the sheet as shown in FIG. 11. As will be observed from FIG. 11 the fiducial marks 24 are not covered by the applied strips. Once the adhesive in the areas 23 has dried, the areas 25 are carefully removed at step 250 leaving a number of elongate separated sections of the original substrate 22, these sections bearing fiducial marks and being held together by multiple series of differently stained strips 26 spanning between the sections.

Figure 12:
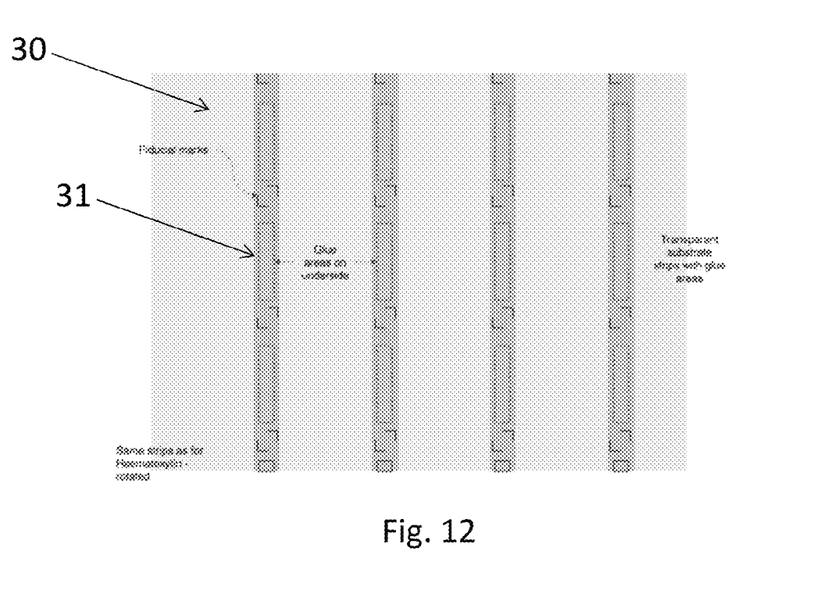
FIG. 12 shows a second base sheet of the second example.
Figure 13:
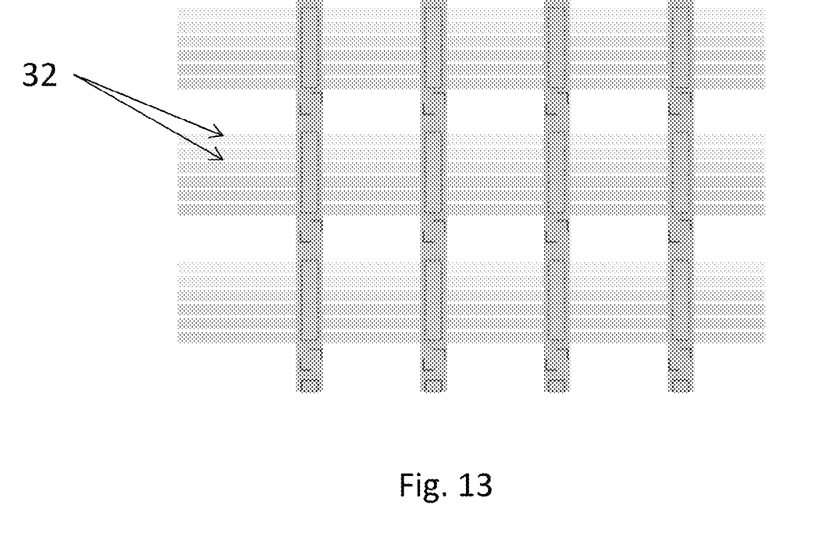
FIG. 13 shows the strips of the second stain applied to the second base sheet.

In a similar way a second sheet 30 of unstained substrate is prepared with glue areas 31 (see FIG. 12), the orientation of the sheet/areas being orthogonal to that of sheet 22. Strips 32 from each sheet of eosin-stained sheets are attached to sheet 30, orientated orthogonally with respect to the strips 26 of sheet 22, and the intervening base sheet material is removed (see FIG. 13).

Figure 14:
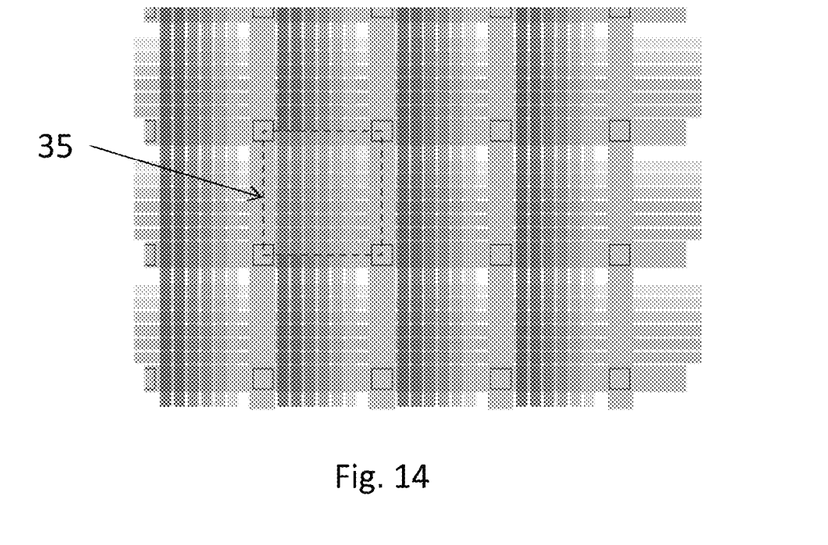
FIG. 14 shows the orthogonal orientation of strips of the first and second series of stains applied together in the second example.
Figure 15:
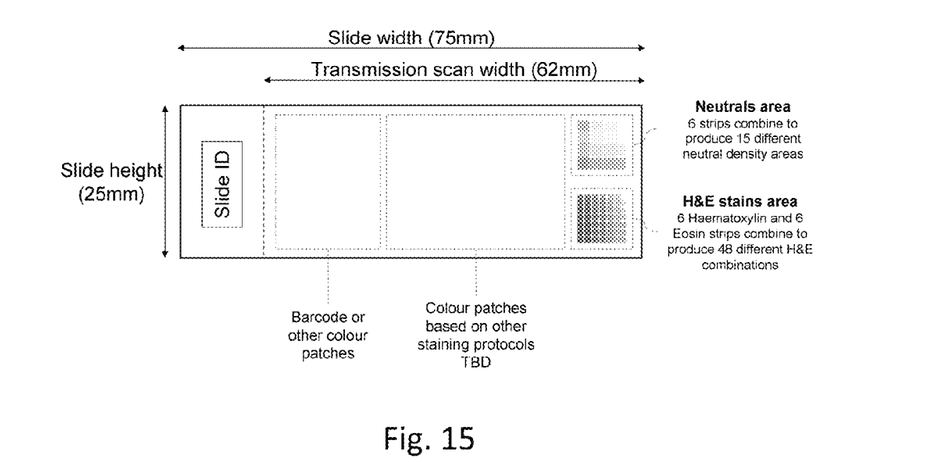
FIG. 15 shows the application of the strips to a microscope slide.

These sets of strips from sheet 30 are then combined (step 270) with those of sheet 22, for example by gluing, as shown in FIG. 14. The fiducial marks provide an easy means to ensure good alignment between these strips due to the transparent nature of the sheets. A section of the resultant structure, such as that highlighted at 35 in FIG. 14 (representing all pairwise combinations of the sheets stained with each stain, plus each sheet stained individually) is then cut from the combined sheet and placed on a microscope slide. Additional sets of sections (such as pairwise combinations of other staining protocols) and other objects such as a barcode that includes measurement data for each stained region (overlapped or individual) may be added before a coverslip is applied to the slide as part of a finishing process for the device. The device may also include a "neutrals area" in which multiple regions are provide which each act as a neutral density filter (providing equal intensity attenuation across the spectrum). The neutrals area is important in the use of the reference device for calibration purposes. The finished device is illustrated in FIG. 15.

The above method produces a very high quality reference or calibration device. In some cases there may exist some slight variations within single sheets in terms of the degree to which they are stained and this leads to slight variation in the colour on the microscope slide. For this reason, when the highest accuracy is needed it is necessary to measure the colour of the stained regions on the slide in situ in the microscope and to make these measurements available to any system that uses the slide for calibration purposes. Care must be taken to ensure that measurements are collected using an optical geometry that is similar to that used when scanning pathology slides.

Figure 16:
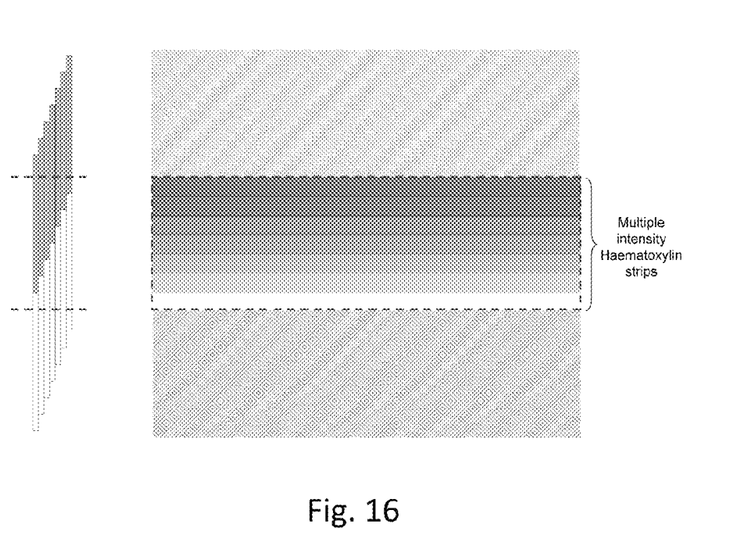
FIG. 16 shows a third example using overlaid strips which are similarly stained.

A third example method is illustrated in FIG. 16. In this case a first step of the method comprises staining a number of similar sheets under identical staining conditions such that a set of identically stained sheets is produced. Then, a series of differently stained regions is obtained by partially overlapping a number of the strips where the intensity of staining in any region is dependent upon the number of strips overlaid for that region. The strips are bonded together to provide a unitary device and the peripheral areas of the device (which do not exhibit a difference in the number of overlaid strips as a function of location) are removed. With this method multiple layers of stained substrate are produce different absorbance for each region as shown. The multiple intensity strips produced in this way are then used as previously to create the set of coloured patches for each staining protocol.

Figure 17:
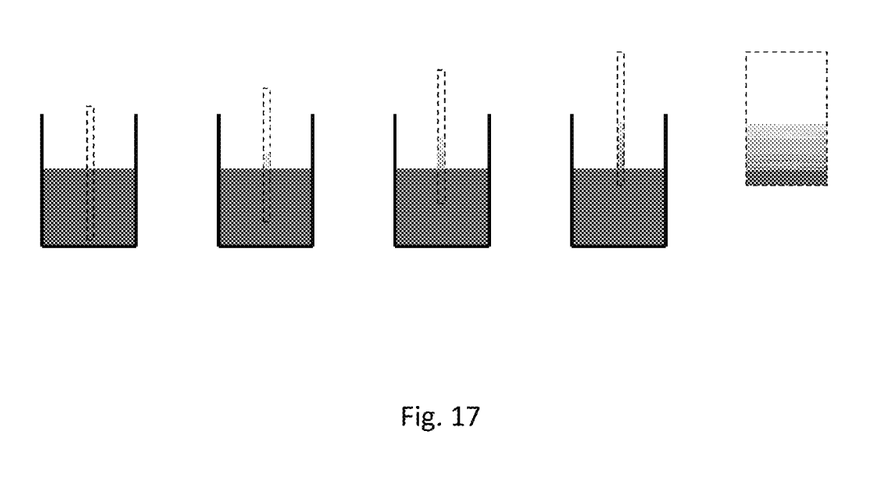
FIG. 17 shows a fourth example method of staining a substrate by staged increases in immersion depth within a liquid stain; and, FIG. 18 shows a fifth example method of staining a substrate by staged removal from a liquid stain.

A fourth example method is illustrated in FIG. 17 for producing a series of stained regions. Here a series of regions having different stain intensities is produced by immersing a single sheet of substrate material in a stain to a first depth and leaving it at this depth for a first period. Thereafter the sheet is immersed further into the stain to a second depth at which it remains for a second period. Further depths are used for corresponding periods until, in this example, four differently stained regions are produced. The stained material bearing the four regions of different staining intensity is illustrated schematically on the right hand side of FIG. 17. The region which was lowermost is provided with the most intense staining since it has endured the longest elapsed time within the stain.

Figure 18:
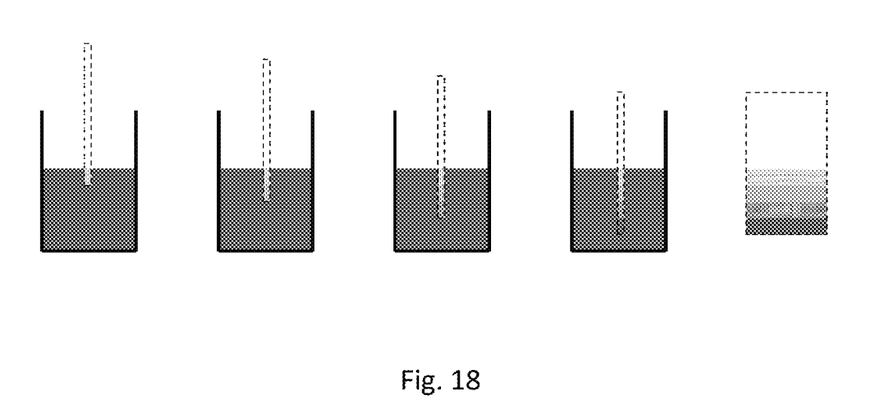

A fifth example method is illustrated in FIG. 18 which is a modification of the fourth example. In this fifth example, the substrate is immersed to a maximum depth initially and is then withdrawn from the stain in a series of reduced depth stages. This results in a similar staining series to that of the fourth example.

The fourth and fifth example methods are particularly beneficial techniques for producing a series of stained regions since the regions are produced within a common piece of substrate film.

The invention claimed is:
1. A method of forming an imaging reference device for a biological material imaging system, the method comprising:
   providing at least one first region of a first substrate, the first substrate being formed from an optically transmissive material which is an analogue of biological tissue, wherein the at least one first region is stained using a first biological tissue stain;
   providing at least one second region of a second substrate, the second substrate being formed from an optically transmissive material which is an analogue of biologi- cal tissue, wherein the at least one second region is stained using a second biological tissue stain; and, overlapping at least one pair of the regions, each pair being formed from the overlap of a first region with a second region, such that light incident upon a pair is modulated by the respective first and second biological tissue stains of the respective regions.

2. A method according to claim 1, wherein a plurality of first regions is provided as a first series of first regions and wherein a plurality of second regions is provided as a second series of second regions.

3. A method according to claim 2, wherein in one or each of the first and second series, the respective spectral effects of the stains applied to the regions within a series are modulated.

4. A method according to claim 3, wherein the modulated spectral effects are effected by using different concentrations of the respective biological tissue stains.

5. A method according to claim 3, wherein the modulated spectral effects are effected by using different time durations of application of the respective biological tissue stains.

6. A method according to claim 3, wherein the modulated spectral effects are caused by using regions of the respective first and/or second substrate having different thicknesses.

7. A method according to claim 3, wherein the modulated spectral effects are caused by using regions of the respective first and/or second substrate having different stain absorption characteristics.

8. A method according to claim 2, wherein each region in one or each of the first or second series is elongate and wherein the directions of elongation of the regions are parallel.

9. A method according to claim 8, wherein the regions of the first and the second series are elongate, wherein the respective directions of elongation of the first and second series are arranged at an angle such that the pairs of overlapping regions form a two dimensional array.

10. A method according to claim 1, wherein one or each of the first substrate or second substrate is provided as a film.

11. A method according to claim 1 wherein the physical arrangement of the regions within the first or second series corresponds to a monotonical modulation in the effect of the respective staining on incident light.

12. A method according to claim 1, wherein the stained regions within a series are formed by the overlap of corresponding numbers of layers of the substrate, each of similar thickness and staining.

13. A method according to claim 1 the first biological tissue stain and the second biological tissue stain comprise one or more different biological tissue stains.

14. A method according to claim 1 wherein the first and second stains are the stains used for one of the following staining protocols:

Haematoxylin and Eosin (H&E), Diaminobenzidine (DAB) with Haematoxylin counter stain, Papanicolaou (PAP), Perls' Prussian blue, Periodic acid-Schiff (PAS), Reticulin, Millers elastic Van Gieson, Shikata, Giemsa stain, Ziehl Neelsen technique, Grocott, Alcian blue PAS, Jones methenamine silver, Gram, Congo red stain for amyloid and Masson trichrome.

15. A method according to claim 1, wherein the one or each of the first and second substrates is formed from a material selected from the group comprising: cellophane, cellulose, agar, agarose and gelatine.

16. A method according to claim 1, further comprising attaching the device to a microscope slide.

17. A method according to claim 1, wherein the staining is provided by immersing the respective first or second substrate in a bath of stain material having a predetermined composition and for a predetermined period.

18. An imaging reference device for a biological material imaging system, the device comprising:

a first substrate formed from an optically transmissive material which is an analogue of biological tissue, the first substrate having at least one first region stained using a first biological tissue stain;

a second substrate formed from an optically transmissive material which is an analogue of biological tissue, the second substrate having at least one second region stained using a first biological tissue stain;

wherein at least one of the first and second regions is overlapped so as to form a pair of regions, such that light incident upon a pair is modulated by the respective first and second biological tissue stains of the respective regions.

19. An imaging reference device according to claim 18, wherein the first and second substrates are connected to each other.

20. An imaging reference device according to claim 18, wherein the device is a calibration device for a biological imaging system.

* * * * *